(12) United States Patent
Lucia et al.

(10) Patent No.: US 6,652,842 B2
(45) Date of Patent: Nov. 25, 2003

(54) DEODORANT COMPOSITIONS COMPRISING DIGLYCEROL

(75) Inventors: Jacqueline Christine Lucia, Wantage Township, NJ (US); Roger E. Stier, Clifton, NJ (US); John Zanone, Montville Township, NJ (US)

(73) Assignee: Noville, Inc., South Hackensack, NJ (US)

( * ) Notice: Subject to any disclaimer, the term of this patent is extended or adjusted under 35 U.S.C. 154(b) by 0 days.

(21) Appl. No.: 10/011,118

(22) Filed: Nov. 13, 2001

(65) Prior Publication Data

US 2003/0103919 A1 Jun. 5, 2003

(51) Int. Cl.$^7$ ............... A61K 7/32; A61K 7/34; A61K 7/38; A61K 7/035
(52) U.S. Cl. ............... 424/65; 424/66; 424/68; 424/69
(58) Field of Search ............... 424/65, 66, 68, 424/69

(56) References Cited

U.S. PATENT DOCUMENTS

| | | |
|---|---|---|
| 2,584,307 A | 2/1952 | Tice |
| 2,975,102 A | 3/1961 | Matsumura et al. |
| 3,523,130 A | 8/1970 | Jones et al. |
| 3,840,656 A | 10/1974 | Kalopissis et al. |
| 3,873,686 A | 3/1975 | Beekman |
| 3,876,758 A | 4/1975 | Beekman |
| 4,556,557 A | 12/1985 | Reichert |
| 4,726,943 A | 2/1988 | Klueppel et al. |
| 4,829,092 A | 5/1989 | Nelson et al. |
| 5,342,617 A | 8/1994 | Gold |
| 5,368,847 A | 11/1994 | Brunetta et al. |
| 5,449,551 A | 9/1995 | Taniguchi |
| 5,456,863 A | 10/1995 | Bergmann |
| 5,474,776 A | 12/1995 | Koyanagi et al. |
| 5,538,720 A | 7/1996 | Jendryssek-Pfaff et al. |
| 5,650,166 A | 7/1997 | Ribier et al. |
| 5,709,849 A | 1/1998 | Ito et al. |
| 5,750,120 A | 5/1998 | Miguel-Colombel |
| 5,874,092 A | 2/1999 | Roulier et al. |
| 5,902,590 A | 5/1999 | Thomas et al. |
| 5,935,384 A | 8/1999 | Taniguchi |
| 5,989,573 A | 11/1999 | Remy |
| 6,001,341 A | 12/1999 | Genova et al. |
| 6,036,968 A | 3/2000 | Roulier et al. |
| 6,042,844 A | 3/2000 | Ishida et al. |
| 6,045,781 A | 4/2000 | Bungard et al. |
| 6,117,434 A | 9/2000 | Oyama et al. |
| 6,126,928 A | * 10/2000 | Swaile |
| 6,146,647 A | 11/2000 | Aoyama et al. |
| 6,180,124 B1 | 1/2001 | Ohta et al. |
| 6,206,902 B1 | 3/2001 | Morikane |
| 6,221,382 B1 | 4/2001 | Ishida et al. |

FOREIGN PATENT DOCUMENTS

| | | |
|---|---|---|
| EP | 0 521 579 | * 7/1993 |
| WO | WO 96/37185 | * 11/1996 |

OTHER PUBLICATIONS

Product Data Sheet—Diglycerol—Solvay Interox web page Apr. 2001.

* cited by examiner

Primary Examiner—Sreeni Padmanabhan
Assistant Examiner—San-ming Hui
(74) Attorney, Agent, or Firm—Norris, McLaughlin & Marcus

(57) ABSTRACT

Cosmetic compositions, particularly solid or gel stick type deodorant compositions, comprising a base solvent system having at least diglycerol, and optionally polyhydric alcohols, and water and gelled with alkali metal salts of saturated fatty acids. The compositions may further comprise monohydric alcohols, surfactants, emollients, fatty alcohols, stabilizing agents, antimicrobial and antibacterial agents, cooling agents, fragrance, dyes and the like. The compositions exhibit improved clarity, enhanced and stronger fragrance impact, and a directional increase in fragrance longevity.

14 Claims, No Drawings

DEODORANT COMPOSITIONS COMPRISING DIGLYCEROL

FIELD OF THE INVENTION

The invention concerns cosmetic compositions, such as deodorant compositions. In a preferred embodiment of the invention, the invention is a stick type cosmetic composition, such as deodorant stick compositions comprising a base solvent system comprising diglycerol, and optionally polyhydric alcohols, and water and gelled with alkali metal salts (e.g. sodium salts) of saturated fatty acids. Preferably, the cosmetic stick compositions are sodium stearate gelled systems. The deodorant compositions of the invention comprising diglycerol exhibit improved clarity, enhanced and stronger fragrance impact, and a directional increase in fragrance longevity. The deodorant compositions may further comprise monohydric alcohols, surfactants, emollients, fatty alcohols, stabilizing agents, antimicrobial agents, cooling agents, fragrance, dyes, pH regulating agents, chelating agents, processing aids and the like.

BACKGROUND OF THE INVENTION

Deodorant compositions having enhanced and stronger fragrance impact and directional increase in fragrance longevity are desired by the consumer. The fragrance masks the malodor that can occur at the axilla as a result of wetness and microbiological activity. Also, particularly in applications where the deodorant composition is in the form of a stick, clarity is desired.

U.S. Pat. No. 6,126,928 describes antiperspirant compositions comprising an amount of antiperspirant active that is dependent on the molecular weight of the polyols used in the antiperspirant compositions. Diglycerol is identified among the myriad of polyols that can be used in these antiperspirant compositions.

Cosmetic compositions linked to the inhibition of body odor comprising alkyl esters combined with carrier agents are described in U.S. Pat. No. 6,001,341. A number of carrying agents are identified for use with the alkyl esters including mono- and poly-hydroxylic alcohols, such as diglycerol. U.S. Pat. No. 4,829,092 describes skin-moisturizing mixtures comprising a humectant having about 90% to 10% glycerol and about 90% to 10% diglycerol. The combination of the glycerol and diglycerol is said to have a synergistic moisturizing effect.

It was an object of the invention to develop cosmetic compositions, and in particular, deodorant compositions having improved clarity.

It was a further object of the invention to develop compositions having stronger fragrance impact and directional increase in fragrance longevity.

It was a further object of the invention to develop compositions having ease of application, improved skin feel (e.g. reduced tackiness and stickiness) and reduced irritation potential.

These and other objectives are achieved by the compositions described herein having a base solvent system comprising at least diglycerol. The compositions have improved clarity. Deodorant compositions comprising diglycerol also have stronger fragrance impact and directional increase in fragrance longevity, as well as ease of application, improved skin feel and reduced irritation potential.

In the present Specification, all parts and percentages are on a weight/weight basis unless otherwise specified.

SUMMARY OF THE INVENTION

The invention pertains to cosmetic compositions, preferably stick-type compositions, such as deodorant stick compositions. The compositions have a base solvent system comprising diglycerol and, optionally, polyhydric alcohols, such as tripropylene glycol and propylene glycol. The compositions further comprise water and are gelled with alkali metal salts of saturated fatty acids, preferably sodium salts. The compositions will, generally, also comprise surfactants, emollients, fatty alcohols, stabilizing agents, antimicrobial agents, coloring agents (dyes), cooling agents, pH regulating agents, chelating agents, additives, fillers and the like, and combinations thereof. Deodorants refer to compositions in final, intermediate and base forms having fragrance or other active compounds to mask odors. This is contrasted with antiperspirant compositions that comprise active compounds that either absorb moisture or prevent excretion from the sweat glands of the human axilla.

The compositions are, preferably, sodium stearate gelled systems. The sodium stearate is used to gel the components of the composition so that the deodorant can be in the form of solid or gel sticks.

DETAILED DESCRIPTION OF THE INVENTION

The invention concerns cosmetic compositions, such as deodorant compositions, having a base solvent system comprising at least diglycerol. While not limiting the scope of the invention, the invention shall now be described in detail with respect to the most preferred embodiment of the invention, that is solid or gel stick-type deodorant compositions.

The deodorant stick-type compositions comprise from about 5% to about 85% of a base solvent system comprising at least diglycerol, about 10% to about 30% water, preferably deionized water, about 1% to about 10% gelling agent, such as sodium stearate, about 0.5% to about 10% surfactant, about 0.1% to about 4% fragrance and about 0.1% to about 1.5% antibacterial active. The compositions may also comprise other fillers and additives, such as emollients, fatty alcohols, stabilizing agents, coloring agents (dyes), cooling agents, processing aids and the like, and combinations thereof. For example, an additive such as crystal inhibitors like stearyl alcohol can be included in the composition to improve stability by reducing crystal formation.

The base solvent system must comprise diglycerol and the deodorant stick-type composition will generally have from about 5% to about 60%, preferably about 15% to about 50%, diglycerol. Diglycerol is a polyol consisting of two molecules of glycerol bonded by an ether linkage and is available from Solvay Interox, Inc., Houston, Tex., USA. Diglycerol is a clear viscous liquid which is larger than most other molecules generally used as humectants or in base solvent systems in deodorant stick-type compositions, as well as other deodorant or cosmetic compositions. Diglycerol is a clear and aesthetically pleasing product which is practically colorless and odorless and very mild to the skin which is desirable compared to propylene glycol, that is traditionally used in deodorant stick-type compositions, which has the drawback of generally being associated with irritation potential. A significant advantage of the invention is the ability to eliminate or reduce the use of propylene glycol in deodorant stick-type compostions as well as other deodorant or cosmetic compositions.

Base solvents used in the invention may further comprise polyhydric alcohols including polyethylene glycol, polypropylene glycol, ethylene glycol, butylene glycol, hexylene glycol, propylene glycol, dipropylene glycol, tripropylene glycol, sorbitol, glycerine and combinations thereof, and monohydric alcohols such as those selected from the group consisting of ethanol, propanol, combinations thereof and the like. A preferred base solvent system comprises diglycerol and propylene glycol and/or tripropylene glycol, and combinations thereof. Generally, when present in the deodorant compositions, the compositions will comprise from about 5% to about 45% propylene glycol and up to about 70%, preferably from about 10% to about 50%, most preferably from about 10% to about 40%, tripropylene glycol.

The selection of glycol in the base solvent system can affect the appearance of the deodorant composition and we have found that the use of diglycerol provides for enhanced clarity, particularly when combining diglycerol with tripropylene glycol and propylene glycol. Although any amount of each compound in the base solvent system is useful in the invention, a base solvent system having a ratio of diglycerol: tripropylene glycol: propylene glycol of from about 3.5:3.5:1 to about 2.2:2.2:1 is particularly useful. Also, a base solvent system comprising diglycerol and propylene glycol, preferably having a ratio of diglycerol: propylene glycol of about 1:0.5 to about 1:1 is useful for the invention. These preferred base solvent systems may be comprised of, consist essentially of or consist of these components. These base solvent systems when consisting essentially of diglycerol and tripropylene glycol and/or propylene glycol will enhance the clarity of any cosmetic composition.

Any gelling agent used in the art of soaps or deodorants may be used in the invention. These gelling agents are generally a metal salt of one or more fatty acids having a chain length of 12–22 carbon atoms. The fatty acid portion of the gelling agent is preferably a relatively pure saturated or unsaturated $C_{12}$–$C_{22}$ fatty acid including myristic, palmitic, stearic, oleic, linoleic, linolenic, and combinations thereof. Preferred gelling agents include sodium stearate, potassium stearate, sodium palmitate, potassium myristate, sodium myristate, combinations thereof and the like, with sodium stearate (available from RTD HallStar Corp. ("RTD HallStar"), Hackettstown, N.J., USA) being most preferred. The gelling agent may be present in the composition at a level of from about 1% to about 10%, preferably about 3% to about 9%, and most preferably from about 4% to about 8%.

Any surfactant acceptable for cosmetic use or topical application may be used, including, by way of non-limiting example, nonionic and anionic surfactants. Suitable nonionic surfactants include those selected from the group consisting of laureth-4, ethoxylated hydrogenated castor oil (such as PEG-40, available from BASF, Mount Olive, N.J., USA), alkyl polyglycoside sodium laureth-13 carboxylate, isosteareth-20, isocetheth-20 and ethoxylated dimethicone copoylol, (such as that available from Goldschmidt A G, Essen, Germany, under the tradename ABIL®). Suitable anionic surfactants include those selected from the group consisting of taurates, sarcosinates, isothionates, sulfosuccinates, derivatives thereof, and the like. Combinations of these nonionic and/or anionic surfactants can be used. Incorporating surfactants into the deodorant sticks is particularly useful to reduce syneresis and to further improve the clarity of the compositions. Emollients include any cosmetic emollients suitable for use in clear glycol base systems.

The fragrance may be selected from the group consisting of any cosmetically acceptable fragrance or fragrances acceptable for topical application. The fragrance should be suitable for masking malodor, such as malodor associated with human sweat. By way of non-limiting examples, these fragrances include those comprising middle note and/or top note volatile constituents, like those selected from the group consisting of allyl amyl glycolate, dihydromyrcenol, aldehyde C-12 MNA, decanol, isobornyl acetate, LILAL®, tricyclo decenyl acetate, benzyl salicylate, and the like, and combinations thereof.

Any antibacterial active acceptable for underarm application can be used in the deodorant compositions. Antibacterial ingredients, by non-limiting example, include those selected from the group consisting of triclosan, bacteriostatic quaternary ammonium compounds such as benzalkonium chloride, benzethonium chloride, cetyl pyridium chloride, lauryl pyridium chloride and methyl benzethonium chloride; triclocarbon; zinc phenol sulfonate; zinc ricinoleate; triethyl citrate; essential oils; and combinations thereof and the like. The most preferred deodorant active is triclosan. The fragrance may also have antibacterial properties.

The deodorant compositions, comprising diglycerol have exemplary clarity, which is particularly important when the deodorant composition is in the form of a clear stick. While not wishing to be bound by any theory, we believe that this may result from the refractive index of diglycerol which is 1.49 compared to clear gels that generally have a refractive index between about 1.44 and about 1.45.

The deodorant compositions exhibit directional increase in fragrance longevity and stronger fragrance impact from the stick. While not wishing to be bound by any theory, we believe that this may result from the size of the diglycerol molecule and its interaction with the fragrance. Because of the size of the diglycerol molecule, it will bind the fragrance after application and because of the relatively slow dissolution rate of diglycerol, the fragrance will be maintained in the deodorant film that is formed upon application of the deodorant. Also, because the diglycerol is a large molecule, the diffusion of the fragrance from the film will be slower.

In addition, the deodorants comprising diglycerol have improved skin feel in that there is less tack and stickiness during and after application. Again, not wishing to be bound by any theory, this may result because diglycerol has emollient properties which give the compositions smooth feel, which may occur because the diglycerol remains on the surface of the skin and acts as a barrier against transepidermal water loss by evaporation. Also, the deodorants comprising diglycerol will have reduced irritation potential because the compositions either do not comprise propylene glycol, or have a reduced amount of propylene glycol, compared to conventional deodorant formulations.

The compositions, particularly deodorant compositions, comprising the base solvent system having at least diglycerol can be made by first combining the diglycerol, and any other components of the base solvent system with water, preferably at elevated temperatures of about 60° C. to about 80° C., and mixing. Next, the gelling agent, such as sodium stearate and optionally other additives, such as stearyl alcohol are added with continued mixing, preferably at the elevated temperatures. Then, the surfactant is added with continued mixing, preferably at the elevated temperatures of about 60° C. to about 80° C., until a uniform mixture is achieved. Finally, the antibacterial active and fragrance are added to the uniform mixture and the composition can be poured into containers. As would be understood to one skilled in the art, the process can be modified slightly to accommodate various components of the base solvent system based on the characteristics of the components and also fillers and additives can be added at any step of the process.

EXAMPLES

Example 1

A deodorant composition having the formulation set forth in Table 1 was prepared.

TABLE 1

| Ingredient | Wt. % |
|---|---|
| Tripropylene Glycol | 28.55 |
| Diglycerol | 30.00 |
| Propylene Glycol | 10.00 |
| Deionized Water | 19.50 |
| Sodium Stearate | 6.00 |
| Stearyl Alcohol | 0.20 |
| Dimethicone Copolyol | 0.50 |
| Triclosan | 0.25 |
| Laureth-4 | 3.00 |
| Fragrance | 2.00 |

The deodorant composition was prepared by first mixing the tripropylene glycol (from Dow Chemical, Midland, Tex., USA), propylene glycol and deionized water in a mixer and then heating this mixture to about 65° C. to about 75° C. and then adding the sodium stearate (from RTD HallStar) and stearyl alcohol (NF from Jeen International, Little Falls, N.J., USA). Next, the diglycerol (from Solvay Interox) was added with mixing at about 65° C. to 75° C. until the mixture was uniform and clear. Dimethicone copolyol (ABIL® B8843 from Goldschmidt A G) and surfactant (Laureth-4 LIPOCOL® L-4 from Lipo Chemicals, Inc.) were added with mixing at about 65° C. to 75° C. until the mixture was uniform. The heat source was then discontinued and the antibacterial active, triclosan (Irgasan DP300 from Ciba Specialty Chemicals Corp., Tarrytown, N.Y., USA) and fragrance were added and the mixture was poured into stick containers. The resulting deodorant composition in the form of a clear stick was observed to be extremely clear and had good stick structure.

Example 2

A deodorant composition having the formulation set forth in Table 2 was prepared.

TABLE 2

| Ingredient | Wt. % |
|---|---|
| Tripropylene Glycol | 31.05 |
| Diglycerol | 30.00 |
| Propylene Glycol | 10.00 |
| Deionized Water | 19.50 |
| Sodium Stearate | 6.00 |
| Stearyl Alcohol | 0.20 |
| Sodium Chloride | 0.50 |
| Dimethicone Copolyol | 0.50 |
| Triclosan | 0.25 |
| Fragrance | 2.00 |

The deodorant composition was prepared by first mixing the tripropylene glycol (from Dow Chemical), propylene glycol and deionized water (17.0% of the formulation) in a mixer and then heating this mixture to about 65° C. to 75° C. and then adding the sodium stearate (RTD OP-100 from RTD Hall Star) and stearyl alcohol (NF from Jeen International) until fully dissolved and clear. Next, sodium chloride (Fine 999 from Morton Salt, Cincinnati, Ohio, USA) that was separately dissolved in deionized water (2.5% of the composition) and the diglycerol (from Solvay Interox) were added with mixing at about 65° C. to 75° C. until the mixture was uniform and clear. Dimethicone copolyol (ABIL® B8843 from Goldschmidt A G) was added with mixing at about 65° C. to 75° C. until the mixture was uniform. The heat source was then discontinued and the antibacterial active, triclosan (Irgasan DP300 from Ciba Specialty Chemicals Corp.) and fragrance were added and the mixture was poured into stick containers. The resulting deodorant composition in the form of a clear stick was observed to be exceptionally clear with no hazing or crystallization.

Example 3

A deodorant composition having the formulation set forth in Table 3 was prepared.

TABLE 3

| Ingredient | Wt. % |
|---|---|
| Tripropylene Glycol | 31.55 |
| Diglycerol | 30.00 |
| Propylene Glycol | 10.00 |
| Deionized Water | 19.50 |
| Sodium Stearate | 6.00 |
| Stearyl Alcohol | 0.20 |
| Dimethicone Copolyol | 0.50 |
| Triclosan | 0.25 |
| Fragrance | 2.00 |

The deodorant composition was prepared by first mixing the tripropylene glycol (from Dow Chemical), propylene glycol and deionized water in a mixer and then heating this mixture to about 65° C. to 75° C. and then adding the sodium stearate (from RTD HallStar) and stearyl alcohol (NF from Jeen International). Next, the diglycerol (from Solvay Interox) was added with mixing at about 65° C. to 75° C. until the mixture was uniform and clear. Dimethicone copolyol (ABIL® B8843 from Goldschmidt A G) was added with mixing at about 65° C. to 75° C. until the mixture was uniform. The heat source was then discontinued and the antibacterial active, triclosan (Irgasan DP300 from Ciba Specialty Chemicals Corp.) and fragrance were added and the mixture was poured into stick containers. The resulting deodorant composition in the form of a clear stick was observed to be clear with no hazing or crystallization.

Example 4

Deodorant compositions having the formulations set forth in Table 4 were prepared. Example 4A is prepared in accordance with the invention, and Example 4B is a comparative example comprising dipropylene glycol and no diglycerol.

TABLE 4

| | Wt. % | |
|---|---|---|
| Ingredient | Example 4A | Example 4B |
| Tripropylene Glycol | 31.05 | 31.05 |
| Dipropylene Glycol | 0.00 | 30.00 |
| Diglycerol | 30.00 | 0 |
| Propylene Glycol | 10.00 | 10.00 |
| Deionized Water | 19.50 | 19.50 |
| Sodium Stearate | 6.00 | 6.00 |

TABLE 4-continued

| | Wt. % | |
|---|---|---|
| Ingredient | Example 4A | Example 4B |
| Stearyl Alcohol | 0.20 | 0.20 |
| Sodium Chloride | 0.50 | 0.50 |
| Dimethicone Copolyol | 0.50 | 0.50 |
| Triclosan | 0.25 | 0.25 |
| Fragrance | 2.00 | 2.00 |

The deodorant compositions were prepared by first mixing the tripropylene glycol (from Dow Chemical), propylene glycol and deionized water (17.0% of the composition) in a mixer and then heating this mixture to about 65° C. to 75° C. and then adding the sodium stearate (from RTD Hall Star) and stearyl alcohol (NF from Jeen International). Next, in Example 4A sodium chloride (Fine 999 from Morton Salt) that was separately dissolved in deionized water (2.5% of the composition) and diglycerol (from Solvay Interox) were added with mixing at about 65° C. to 75° C. until the mixture was uniform and clear, and in Example 4B salt solution and dipropylene glycol were added with mixing at about 65° C. to 75° C. until the mixture was uniform. Next, dimethicone copolyol (ABIL® B8843 from Goldschmidt AG) was added with mixing at about 65° C. to 75° C. until the mixture was uniform. The heat source was then discontinued and the antibacterial active, triclosan (Irgasan DP300 from Ciba Specialty Chemicals Corp.) and fragrance were added and the mixture was poured into stick containers and packaged.

The deodorant sticks were observed for optical clarity. The stick prepared with diglycerol (Example 4A) had excellent clarity, however, the comparative formulation (Example 4B) was opaque and white in color.

Examples 4A and 4B were evaluated for fragrance strength from the package and impact on skin (at initial application). The evaluation was performed by sensory perception of each stick when immediately opening the package and upon initial application to the skin (impact on skin). The stick of Example 4A had better fragrance strength and impact on skin than Example 4B.

Sticks of Examples 4A and 4B were subjected to a six hour blind fragrance study using eight expert panelists. An expert panelist is trained in sensory perception. Examples 4A and 4B were applied to a forearm, and the panelists did not know which sample was applied to which forearm. Each panelist was asked to record which forearm had the greater fragrance intensity, or an equal amount, at application and at 1, 3 and 6 hours after application. The results are set forth in Table 5, below. At application and at 1 hour and 3 hours, five panelists reported that Example 4A had the greatest fragrance intensity, and at 6 hours all eight panelists reported that Example 4A had the greatest fragrance intensity.

TABLE 5

| TIME AFTER APPLICATION | | 0 HOUR | 1 HOUR | 3 HOURS | 6 HOURS |
|---|---|---|---|---|---|
| Number of Panelist Reporting | Example 4A Having Greater Fragrance Intensity | 5 | 5 | 5 | 8 |
| | Example 4B Having Greater Fragrance Intensity | 1 | 2 | 2 | 0 |
| | Equal Fragrance Intensity | 2 | 1 | 0 | 0 |

Example 5

A deodorant composition having the formulation set forth in Table 6 was prepared.

TABLE 6

| Ingredient | Wt. % |
|---|---|
| Tripropylene Glycol | 28.55 |
| Diglycerol | 30.00 |
| Propylene Glycol | 10.00 |
| Deionized Water | 19.50 |
| Sodium Stearate | 6.00 |
| Stearyl Alcohol | 0.20 |
| Dimethicone Copolyol | 0.50 |
| Triclosan | 0.25 |
| Laureth-4 | 3.00 |
| Fragrance | 2.00 |

The deodorant composition was prepared by first mixing the tripropylene glycol (from Dow Chemical), propylene glycol and deionized water in a mixer and then heating this mixture to about 65° C. to 75° C. and then adding the sodium stearate (RTD OP-100 from RTD Hall Star) and stearyl alcohol (NF from Jeen International). Next, the diglycerol (from Solvay Interox) was added with mixing at about 65° C. to 75° C. until the mixture was uniform and clear. Dimethicone copolyol (ABIL® B8843 from Goldschmidt A G) and surfactant (Laureth-4, LIPOCOL® L-4 from Lipo Chemicals, Inc.) were added with mixing at about 65° C. to 75° C. until the mixture was uniform. The heat source was then discontinued and the antibacterial active, triclosan (Irgasan DP300 from Ciba Specialty Chemicals Corp.) and fragrance were added and the mixture was poured into stick containers.

The resulting deodorant composition in the form of a clear stick was observed for clarity at about 48 hours and again at about 72 hours. The sticks were observed to be extremely clear and had good stick structure when made. The sticks maintained clarity after about 48 hours and after about 72 hours.

What is claimed is:

1. A deodorant composition comprising from about 5% to about 85% by weight of a base solvent system consisting essentially of diglycerol, tripropylene glycol and propylene glycol having a ratio of diglycerol: tripropylene glycol: propylene glycol of from about 3.5:3.5:1 to about 2.2:2.2:1, about 10% to about 30% by weight water, about 1% to about 10% by weight gelling agent, about 0.5% to about 10% by weight surfactant, about 0.1% to about 4% by weight fragrance and about 0.1% to about 1.5% by weight antibacterial active.

2. The deodorant composition of claim 1 further comprising fillers and additives selected from the group consisting of emollients, fatty alcohols, stabilizing agents, coloring agents, cooling agents, crystal inhibitors, pH regulating agents, chelating agents, processing aids and combinations thereof.

3. The deodorant composition of claim 2 wherein the crystal inhibitor is stearyl alcohol.

4. The deodorant composition of claim 1 wherein the base solvent system has from about 5% to about 60% by weight diglycerol, from about 5% to about 45% by weight propylene glycol and from about 10% to about 50% by weight tripropylene glycol.

5. The deodorant composition of claim 1 wherein the base solvent system further consists of polyhydric alcohols and/or monohydric alcohols selected from the group consisting of polyethylene glycol, polypropylene glycol, ethylene glycol, butylene glycol, hexylene glycol, dipropylene glycol, sorbitol, glycerine, ethanol, propanol and combinations thereof.

6. The deodorant composition of claim 1 wherein the gelling agent is a metal salt of one or more fatty acids having a chain length of 12–22 carbon atoms.

7. The deodorant composition of claim 6 wherein the fatty acid is selected from the group consisting of myristic, palmitic, stearic, oleic, linoleic, linolenic, and combinations thereof.

8. The deodorant composition of claim 6 wherein the metal salt of one or more fatty acids is selected from the group consisting of sodium stearate, potassium stearate, sodium palmitate, potassium myristate, sodium myristate and combinations thereof.

9. The deodorant composition of claim 1 wherein the surfactant is selected from the group consisting of laureth-4, ethoxylated hydrogenated castor oil, alkyl polyglycoside, sodium laureth-13 isoseareth 20, carboxylate isocetheth-20, ethoxylated dimethicone copolyl and combinations thereof.

10. The deodorant composition of claim 1 wherein the surfactant is selected from the group consisting of taurates, sarcosinates, isothionates, sulfosuccinates, and combinations thereof.

11. The deodorant composition of claim 1 wherein the fragrance is selected from the group consisting of a cosmetically acceptable fragrance or a fragrance acceptable for topical application.

12. The deodorant composition of claim 1 wherein the antibacterial active is triclosan, bacteriostatic quaternary ammonium compounds, triclocarbon, zinc phenol sulfonate, zinc ricinoleate, triethyl citrate, essential oils, and combinations thereof.

13. The deodorant composition of claim 12 wherein the bacteriostatic quaternary ammonium compounds are selected from the group consisting of benzalkonium chloride, benzethonium chloride, cetyl pyridium chloride, lauryl pyridium chloride, methyl benzethonium chloride and combinations thereof.

14. The deodorant composition of claim 1 in the form of a solid or gel stick.

* * * * *